(12) United States Patent
Rahme et al.

(10) Patent No.: US 10,387,196 B2
(45) Date of Patent: Aug. 20, 2019

(54) MEDICAL IMAGING DISTRIBUTION SYSTEM AND DEVICE

(71) Applicant: Imaging Advantage LLC, Phoenix, AZ (US)

(72) Inventors: Kamil Rahme, Phoenix, AZ (US); Jordan Kajouharov, Scottsdale, AZ (US)

(73) Assignee: IMAGING ADVANTAGE LLC, Plantation, FL (US)

( * ) Notice: Subject to any disclaimer, the term of this patent is extended or adjusted under 35 U.S.C. 154(b) by 219 days.

(21) Appl. No.: 15/489,993

(22) Filed: Apr. 18, 2017

(65) Prior Publication Data

US 2017/0300358 A1    Oct. 19, 2017

Related U.S. Application Data (60) Provisional application No. 62/324,271, filed on Apr. 18, 2016, provisional application No. 62/324,273, filed on Apr. 18, 2016.

(51) Int. Cl.

| | |
|---|---|
| *G06F 9/46* | (2006.01) |
| *G06F 9/48* | (2006.01) |
| *A61B 6/00* | (2006.01) |
| *A61B 8/00* | (2006.01) |
| *G06F 16/58* | (2019.01) |
| *G06F 19/00* | (2018.01) |
| *G16H 15/00* | (2018.01) |
| *A61B 1/00* | (2006.01) |

(52) U.S. Cl.
CPC ............ *G06F 9/4881* (2013.01); *A61B 6/563* (2013.01); *A61B 8/565* (2013.01); *G06F 16/5866* (2019.01); *G06F 19/321* (2013.01); *G16H 15/00* (2018.01); *A61B 1/00011* (2013.01)

(58) Field of Classification Search
None
See application file for complete search history.

(56) References Cited

U.S. PATENT DOCUMENTS

2015/0154778 A1*   6/2015   Hughes .................. G06F 19/321
                                                                    345/629

* cited by examiner

*Primary Examiner* — Gregory A Kessler
(74) *Attorney, Agent, or Firm* — Kilpatrick Townsend & Stockton LLP (57) ABSTRACT

Improved systems and devices for medical imaging distribution are provided. A medical imaging order may be received from a medical facility that includes medical imaging. A configuration may be selected and applied based on a body site and an urgency field associated with the order that defines queueing rules for the medical imaging order. Utilization factors for queues associated with radiologists may also be determined. The configuration and the utilization factors may be used to determine a subset of queues associated with a subset of radiologists. The subset of queues may be prioritized based on certain requirements, such as how many medical imaging reports a particular radiologist is required to review, how many medical imaging reports are required to be allocated to a particular radiologist, and the like. The highest prioritized queue may be selected and the medical imaging order may be transmitted to the radiologist associated with that queue.

21 Claims, 8 Drawing Sheets

FIG. 8

MEDICAL IMAGING DISTRIBUTION SYSTEM AND DEVICE

CROSS-REFERENCES TO RELATED APPLICATIONS

This application claims the benefit of U.S. Provisional Patent Application No. 62/324,271, filed Apr. 18, 2016, entitled "MEDICAL IMAGING DISTRIBUTION SYSTEM AND DEVICE", and is hereby incorporated by reference in its entirety. This application further claims the benefit of U.S. Provisional Patent Application No. 62/324,273, filed Apr. 18, 2016, entitled "PRE-CACHING OF RELATED MEDICAL IMAGING", and is hereby incorporated by reference in its entirety. This application is further related to U.S. patent application Ser. No. 15/489,996, filed Apr. 18, 2017, entitled "SYSTEM AND DEVICE FOR PRE-CACHING OF RELATED MEDICAL IMAGING", and is hereby incorporated by reference in its entirety.

BACKGROUND OF THE INVENTION

Medical facilities, including hospitals and clinics, implement a variety of medical imaging systems, such as X-rays, CTs, MRIs, ultrasounds, and the like, to create medical images of patients. These medical images may be combined with patient information (e.g., name, date of birth, historical medical records, etc.) as well as imaging information (e.g., type of imaging, body location of imaging, name and location of medical facility, etc.) to create EMRs (electronic medical records). The EMRs may then be sent to radiologists, who may analyze and interpret the medical images. The radiologists may generate a medical imaging report including analysis and information (e.g., diagnoses, findings, conclusions, radiologist name, date and time of diagnoses, comments, etc.) that may be forwarded back to the medical facilities for appropriate treatment of the patients.

Implementing these processes may give rise to a variety of obstacles. For example, medical facilities may only have access to a limited number of radiologists on site. Thus, often times, the radiologist analyzing the medical imaging and generating the medical imaging report may be remote (i.e., offsite) from the medical facility where the medical images were generated. The medical imaging may be allocated to the remote radiologists in the order that they are received from the medical facilities, potentially resulting in large queues of medical imaging waiting to be reviewed by slower radiologists. Because the turnaround time for having the medical imaging analyzed may be critical in some cases, any delay in receiving the medical imaging report may impact patient care.

SUMMARY OF THE INVENTION

Thus, according to some embodiments of the invention, improved systems and devices for medical imaging distribution are provided. According to some embodiments of the invention, a medical imaging order may be received from a medical facility that includes medical imaging (e.g., an X-ray, ultrasound, CT scan, MRI, etc.). The medical imaging order may also include parameters, such as a body site that was imaged and a field defining urgency of the medical imaging order. A configuration may be selected and applied based on the body site and the field that defines queueing rules for the medical imaging order. Utilization factors for queues associated with radiologists may also be determined (e.g., receipt speed, connection speed, review speed, etc.). The configuration and the utilization factors may be used to determine a subset of queues associated with a subset of radiologists. The subset of queues may be prioritized based on certain requirements, such as how many medical imaging reports a particular radiologist is required to review, how many medical imaging reports are required to be allocated to a particular radiologist, and the like. The highest prioritized queue may be selected and the medical imaging order may be transmitted to the radiologist associated with that queue.

According to some embodiments of the invention, a device for organizing radiological imaging queues at scale is provided. The device comprises a processor and a memory coupled to the processor. The memory stores instructions, which when executed by the processor, cause the device to perform operations including receiving, by a network interface of a device in a network, a request to generate a report file. The request includes at least one image file and a plurality of parameters. The plurality of parameters include a site that is imaged in the at least one image field and a field defining urgency of the report file. The request is received from a first node external to the device in the network. The operations further include extracting the site and the field from the request. The operations further include selecting and retrieving, from a second node internal to the device, a configuration describing a plurality of queueing rules to be executed on the plurality of parameters of the request. The configuration is selected based on the site and the field. The operations further include determining a plurality of utilization factors for a plurality of queues. The operations further include processing the configuration and the plurality of utilization factors to determine a subset of queues of the plurality of queues. Processing the configuration includes executing the plurality of queueing rules on the plurality of parameters included in the request. The subset of queues is associated with a prioritization that ranks the subset of queues according to requirements of the device to select each queue and requirements of the subset of queues to stage report files. The operations further include selecting a queue from the subset of queues based on the prioritization. The operations further include allocating the request to the queue. The operations further include transmitting the request to a third node external to the device in the network to generate the report file. The third node is associated with the queue. The report file includes the at least one image file and at least one medical notation.

According to some embodiments of the invention, a computer-implemented method is provided. The method comprises receiving, by a network interface of a server in a network, a request to generate a report file. The request includes at least one image file and a plurality of parameters. The plurality of parameters include a site that is imaged in the at least one image field and a field defining urgency of the report file. The request is received from a first node external to the server in the network. The method further comprises extracting the site and the field from the request. The method further comprises selecting and retrieving, from a second node internal to the server, a configuration describing a plurality of queueing rules to be executed on the plurality of parameters of the request. The configuration is selected based on the site and the field. The operations further include determining a plurality of utilization factors for a plurality of queues. The method further comprises processing the configuration and the plurality of utilization factors to determine a subset of queues of the plurality of queues. Processing the configuration includes executing the plurality of queueing rules on the plurality of parameters included in the request. The subset of queues is associated with a prioritization that ranks the subset of queues according to requirements of the server to select each queue and requirements of the subset of queues to stage report files. The method further comprises selecting a queue from the subset of queues based on the prioritization. The method further comprises allocating the request to the queue. The method further comprises transmitting the request to a third node external to the server in the network to generate the report file. The third node is associated with the queue. The report file includes the at least one image file and at least one medical notation.

According to some embodiments of the invention, a computer-program product tangibly embodied in a non-transitory machine-readable storage medium of a computing device is provided. The non-transitory machine-readable storage medium includes instructions that, when executed by one or more processors, cause the one or more processors to receive, by a network interface of the computing device in a network, a request to generate a report file. The request includes at least one image file and a plurality of parameters. The plurality of parameters include a site that is imaged in the at least one image field and a field defining urgency of the report file. The request is received from a first node external to the computing device in the network. The instructions further cause the one or more processors to extract the site and the field from the request. The instructions further cause the one or more processors to select and retrieve, from a second node internal to the computing device, a configuration describing a plurality of queueing rules to be executed on the plurality of parameters of the request. The configuration is selected based on the site and the field. The instructions further cause the one or more processors to determine a plurality of utilization factors for a plurality of queues. The instructions further cause the one or more processors to process the configuration and the plurality of utilization factors to determine a subset of queues of the plurality of queues. Processing the configuration includes executing the plurality of queueing rules on the plurality of parameters included in the request. The subset of queues is associated with a prioritization that ranks the subset of queues according to requirements of the device to select each queue and requirements of the subset of queues to stage report files. The instructions further cause the one or more processors to select a queue from the subset of queues based on the prioritization. The instructions further cause the one or more processors to allocate the request to the queue. The instructions further cause the one or more processors to transmit the request to a third node external to the device in the network to generate the report file. The third node is associated with the queue. The report file includes the at least one image file and at least one medical notation.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

Illustrative embodiments of the present invention are described in detail below with reference to the following drawing figures.

DETAILED DESCRIPTION OF THE INVENTION

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the invention. However, it will be apparent that various embodiments may be practiced without these specific details. The figures and description are not intended to be restrictive.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium. A processor(s) may perform the necessary tasks.

Figure 1:
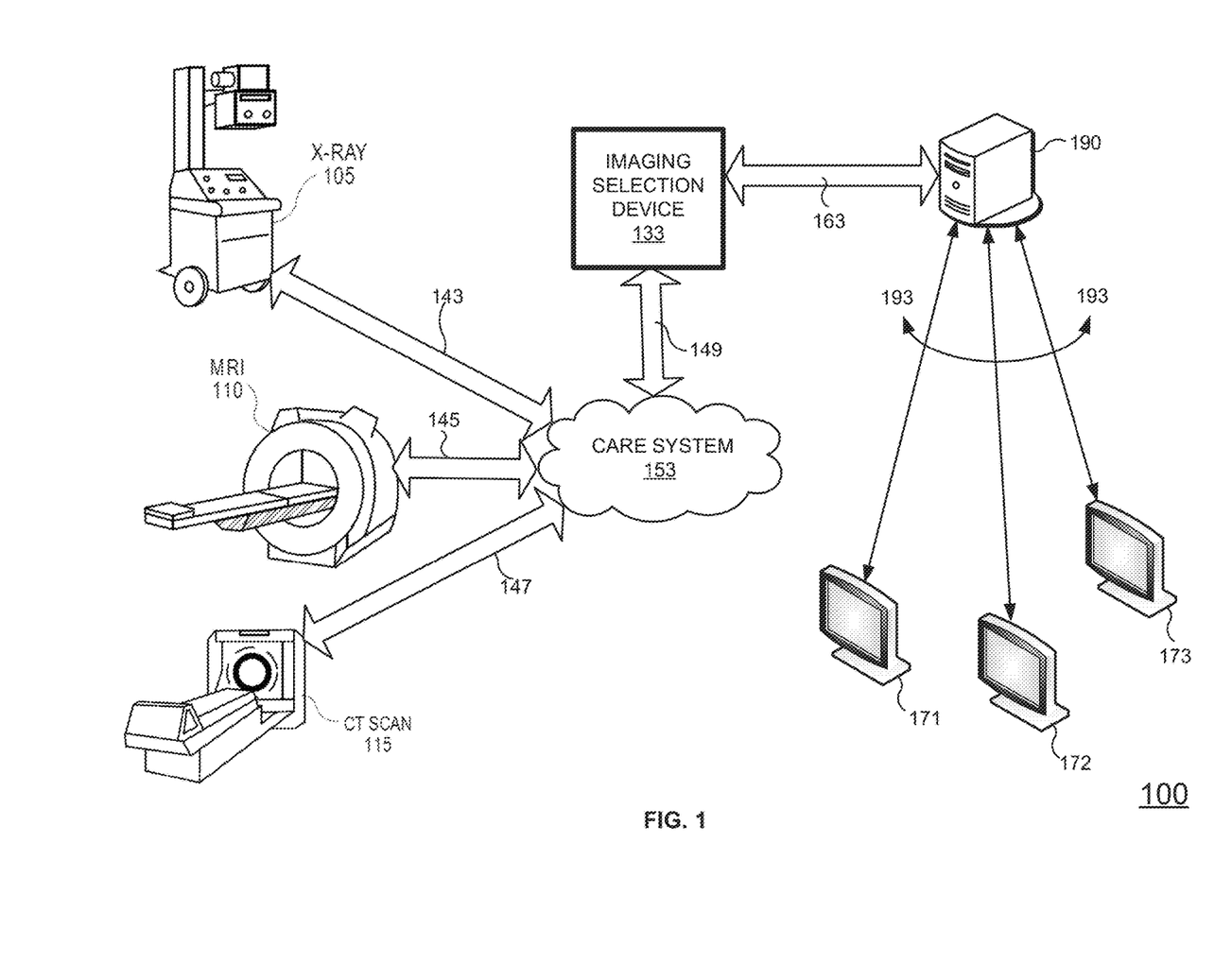
FIG. 1 is a system diagram illustrating a medical imaging distribution system according to some embodiments of the invention.

FIG. 1 illustrates a system 100 for distributing EMRs (electronic medical records) that include medical imaging. System 100 includes medical imaging devices. The medical imaging devices may include, but are not limited to, X-ray device 105, MRI device 110, and CT scan device 115. Other types of medical imaging devices (not shown) include ultrasound devices, endoscopy devices, elastography devices, tactile imaging devices, thermography devices, medical photography devices, nuclear medicine functional imaging devices (e.g., positron emission tomography (PET) devices, single-photo emission computed tomography (SPECT) devices, etc.), and/or the like. System 100 also includes care system 153, imaging selection device 133, distribution device 190, and radiology terminals 171, 172, and 173.

In the illustrated embodiment, X-ray device 105 is networked to care system 153 via link 143. Similarly, MRI device 110 is networked to care system 153 via link 145 and CT scan device 115 is networked to care system 153 via link 147. Links 143, 145, 147 may include Ethernet connections, wireless connections, or any other suitable network and/or networking protocol. For example, links 143, 145, 147 may be implemented as part of a personal area network (PAN), a local area network (LAN), a metropolitan area network (MAN), a wide area network (WAN), a storage area network (SAN), an enterprise private network (EPN), a virtual private network (VPN), and/or the like. Links 143, 145, 147 may represent communication via any suitable network protocol, such as WiFi/WiMAX, Bluetooth, fibre channel network protocols, TCP/IP, OSI, SSH, SMB, FTP, SMTP, HTTP, HTTPs, SSL, SFTP, and/or the like.

Care system 153 may include a networked datastore suitable to store EMRs, medical imaging, patient information, and the like, such as network-attached storage (NAS) or the like. Care system 153 may include, for example, EMR storage, a Picture Archiving and Communication System (PACS), a Radiology Information System (RIS), and/or the like, as discussed further herein. In some embodiments, care system 153 is a data storage server connected to a network that provides access to EMRs and other records by clients, such as medical facilities, doctors, patients, caregivers, and/or radiologists. Care system 153 may provide access to EMRs and other records using network file sharing protocols such as Network File System (NFS) protocol, Server Message Block (SMB)/Common Internet File System (CIFS) protocol, Apple Filing Protocol (AFP), combinations thereof, and/or the like. Care system 153 may include redundant memory backups to ensure the integrity of the EMRs. The networked datastore may have Terabytes of storage, for example. Care system 153 may include, for example, primary storage, secondary storage, tertiary storage, and/or offline storage. Care system 153 may further include processors, in some embodiments.

Imaging selection device 133 is configured to access care system 153 and medical imaging stored in care system 153. Imaging selection device 133 is configured to read EMRs stored in care system 153 as well as write to EMRs stored in care system 153 via link 149. Link 149 may include Ethernet connections, wireless connections, or other suitable networking protocol that facilitates read and/or write access to the particular care system 153.

X-ray device 105, MRI device 110, CT scan device 115, care system 153, and imaging selection device 133 may all be included in a same medical facility such as a hospital or clinic. Alternatively, the medical imaging devices may be in use at more than one clinic while care system 153 is not co-located at the same physical site of the medical imaging devices. In other words, care system 153 may be located locally or remotely with respect to a medical facility. It is contemplated that more than one care system 153 may be implemented in some embodiments.

Imaging selection device 133 is configured to access medical imaging files within care system 153 as well as certain medical data that is germane to analyzing medical imaging. Some medical data that is included in EMRs stored in care system 153 is not germane to medical imaging files. For example, a patient's social security number is not necessarily useful in analyzing medical imaging. Imaging selection device 133 sends medical imaging files and other relevant medical data that is relevant to analyzing medical imaging to distribution device 190, via link 163. Distribution device 190 may be a cloud server physically located at a datacenter in some embodiments. System 100 may include more than one distribution device 190 that are stored in different regional locales, for example. Imaging selection device 133 may access the distribution device 190 that is within closest physical proximity to the imaging selection device 133 in some embodiments. In some embodiments, imaging selection device 133 may select a distribution device 190 according to some other criteria, such as network traffic at particular distribution devices 190.

In some embodiments, imaging selection device 133 may generate a request (also referred to herein as an "order") for a medical imaging report (also referred to herein as a "report file"). The medical imaging report may include at least one image file (also referred to herein as "medical imaging") and one or more parameters. The parameters may be stored as metadata of the image file in some embodiments. The parameters may include descriptors of the image file, the request, and/or the medical imaging report, such as a body site that is imaged in the image file and a field defining urgency of the report file (e.g., how quickly the medical imaging report is needed).

In some embodiments, distribution device 190 receives the medical images and other relevant medical data and generates the request to be put into a queue. The request is assigned to a radiologist and then transferred to the device/system (e.g. 171, 172, or 173) used by the assigned radiologist via one of network links 193. The server may assign the task to a certain radiologist based on radiology specialty (e.g., neurology, oncology, etc.), radiologist availability, a number of tasks already in a radiologist queue, or a variety of other factors, as discussed further herein.

In either embodiment, the assigned radiologist will generate a report based on viewing the medical images and corresponding relevant medical data and send the report back to distribution device 190, via link 193. Distribution device 190 transmits the report back to imaging selection device 133. The report may be in a designated (e.g., standardized) format for efficient processing by imaging selection device 133. Imaging selection device 133 stores the report in care system 153 so that it is accessible for health care providers, facilities, caregivers, patients, etc., that may have access to care system 153.

Figure 2:
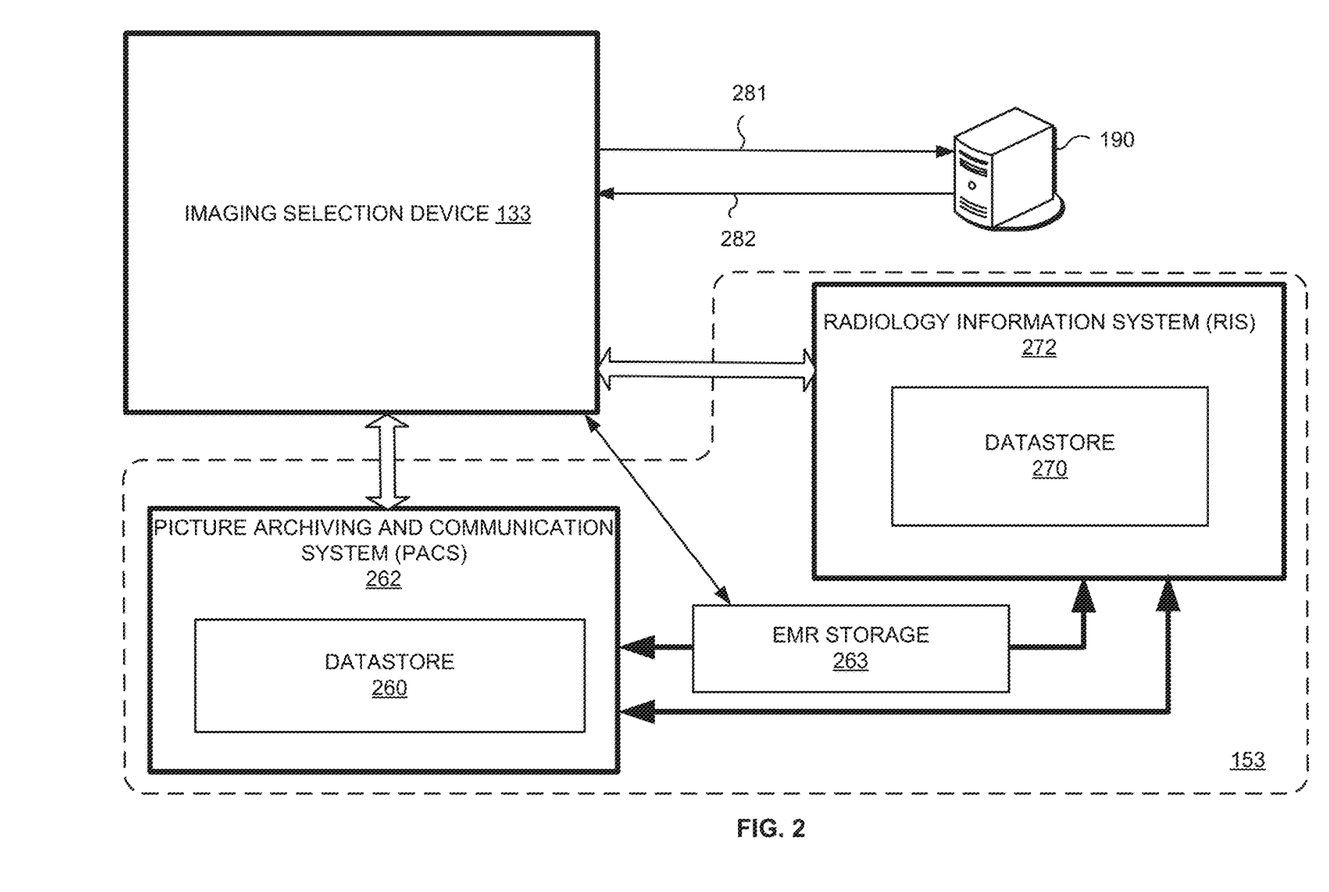
FIG. 2 is a system diagram illustrating a medical imaging report distribution system according to some embodiments of the invention.

FIG. 2 illustrates a system for distributing medical imaging records (e.g., medical images, EMRs, requests for medical imaging reports, etc.) that include medical imaging. The system includes an exemplary imaging selection device 133 in communication with a distribution device 190 (also referred to herein as a "hub"). The system also includes care system 153. Care system 153 may include, for example, a Picture Archiving and Communication Systems (PACS), EMR storage 263, and/or a Radiology Information System (RIS) 272. As appreciated by one skilled in the art, one, none or multiple of each of these components may exist in care system 153. For example, there may be one RIS 272 per medical imaging device (e.g., X-ray device, MM device, etc.) at a given medical imaging facility, one PACS 262 per medical imaging facility, and one remote EMR storage 263 located in the cloud.

In use, the imaging selection device 133 may receive medical imaging for a patient from a RIS 272 of a particular medical imaging device, and/or from PACS 262 of a particular medical imaging facility. The medical imaging may be stored in datastore 260 of PACS 262 and/or datastore 270 of RIS 272. In another example, the imaging selection device 133 may receive medical imaging for a patient as part of an EMR stored in EMR storage 263. In some embodiments, PACS 262 and RIS 272 may have access to one another by a link to augment the respective medical records utilizing data from the other system.

In response to receiving medical imaging for a patient, the imaging selection device 133 may request additional medical records from PACS 262, RIS 272, and/or EMR storage 263 that are relevant to the medical imaging to create a full study profile for the patient. The full study profile may include the initially received medical imaging and/or some or all of the additional medical records. For example, if the medical imaging received is for a left knee of a patient, the imaging selection device 133 may request all previous medical imaging made of the left knee of the patient in the patient's history, as well as any other relevant information (e.g., prior diagnoses, prior surgeries, prescribed medications, physical therapy records, etc.). The additional medical records may be retrieved by using one or more identifiers included in the initially received medical imaging, such as a patient's name, a patient's date of birth, a patient identification number, and/or the like.

The imaging selection device 133 may then filter and format the study profile. The imaging selection device 133 may transmit the study profile 281 to the distribution device 190. The distribution device 190 may receive the study profile 281 and append it to a request for a medical imaging report. In other words, the request may include the study profile 281. The request may be assigned to a radiologist and then transferred to the device (e.g., 171, 172, and/or 173) used by the assigned radiologist via one of network links 193, as shown in FIG. 1. The assigned radiologist may generate a report file based on viewing the medical images included in the request and send a report file 282 back to distribution device 190. Distribution device 190 may transmit report file 282 back to imaging selection device 133. Report file 282 may include an identifier that identifies the patient or file that the imaging package originates from (e.g., a patient or record identification number, a patient name, a patient date of birth, and/or the like). The report file 282 may be in a designated format for efficient processing by imaging selection device 233, such as a standardized format. The report file 282 may be translated into a storing format that can be written back to the care system 153. Writing the translated report to the care system 153 may include accessing the identifier so that the correct patient's EMR can be updated with the report from the radiologist. The identifier may be any combination of letters, numbers, graphics, and/or symbols.

Imaging selection device 133, the components of care system 153, and/or medical imaging distribution device 190 may use any suitable number of subsystems to facilitate the functions described herein. Such subsystems or components may be interconnected via a system bus. Subsystems may include a printer, keyboard, fixed disk (or other memory comprising computer readable media), display, which may be coupled to a display adapter, and others. Peripherals and input/output (I/O) devices, which may couple to an I/O controller, can be connected to the imaging selection device 133, the components of care system 153, and/or medical imaging distribution device 190 by any number of means. For example, an external interface can be used to connect the imaging selection device 133, the components of care system 153, and/or distribution device 190 to a WAN such as the Internet, input device, or a scanner. The interconnection via the system bus may allow the central processor to communicate with each subsystem and to control the execution of instructions from system memory or the fixed disk, as well as the exchange of information between subsystems. The system memory and/or the fixed disk may embody a computer-readable medium.

The functions of imaging selection device 133, the components of care system 153, and/or distribution device 190 described herein may be implemented as software code to be executed by a processor using any suitable computer language such as, for example, Java, C++, or Perl, using, for example, conventional or object-oriented techniques. The software code may be stored as a series of instructions or commands on a computer-readable medium, such as a random access memory (RAM), a read only memory (ROM), a magnetic medium such as a hard drive or a floppy disk, and/or an optical medium such as a CD-ROM. The computer readable medium may be any combination of such storage or transmission devices.

Such programs may also be encoded and transmitted using carrier signals adapted for transmission via wired, optical and/or wireless networks conforming to a variety of protocols, including the Internet. As such, a computer-readable medium according to an embodiment of the present invention may be created using a data signal encoded with such programs. Computer-readable media encoded with the program code may be packaged with a compatible device or provided separately from other devices (e.g., via Internet download). Any such computer-readable medium may reside on or within a single computer product (e.g., a hard drive a CD, or an entire computer system), and may be present on or within different computer products within a system or network. The systems may include a display for providing any of the results described herein to a user.

Figure 3:
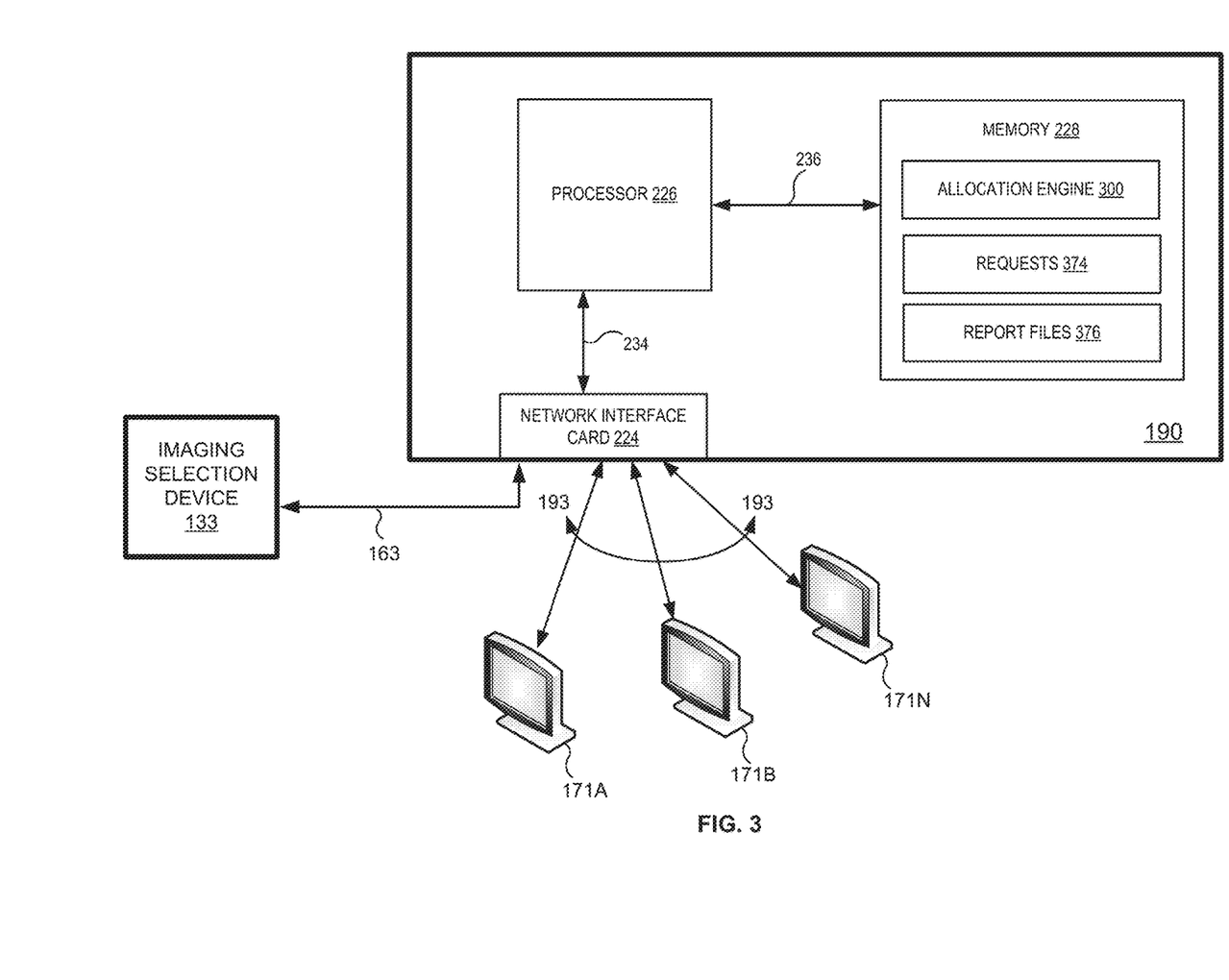
FIG. 3 is a system diagram illustrating a distribution device according to some embodiments of the invention.

FIG. 3 is a system diagram illustrating the details of a distribution device 190 according to some embodiments of the invention. Distribution device 190 may be communicatively coupled to imaging selection device 133 via link 163 and a plurality of radiologist computers 171A, 171B, 171N via links 193. Although shown and described as being coupled to three radiologist computers 171A, 171B, 171N, it is contemplated that distribution device 190 may be coupled to any number of radiologist computers.

Distribution device 190 may include memory 228 (e.g., a computer-readable medium) that includes an allocation engine 300, requests 374, and report files 376. The allocation engine 300, requests 374, and/or report files 376 may be stored in one or more volatile or nonvolatile datastores associated with the distribution device 190. These datastores may be internal or external to the distribution device 190. Distribution device 190 may also include a processor 226. The processor 226 may include a microprocessor, FPGA, or any other suitable logic device. The processor 226 may interface with the memory 228 over a PCI (Peripheral Component Interface) bus 236, for example.

Distribution device 190 may also include a network interface card 224 or any other suitable networking hardware (e.g., an Ethernet card or 802.11 WiFi card) to interface with the imaging selection device 133 and the radiologist computers 171A, 171B, 171N. The network interface card 224 may interface with the processor 226 over a PCI (Peripheral Component Interface) bus 234, for example. The network interface card 224 may interface with imaging selection device 133 to access medical imaging records (e.g., EMRs, medical imaging, requests for medical imaging reports, other medical records, etc.) that are stored on one or more datastores of the imaging selection device 133. In some embodiments, the medical imaging may be compressed for transmission. The compression may be lossless compression, in one embodiment. Possible compression modes include JPLL (JPEG lossless), JLSL (JPEG-LS Lossless), J2KR (JPEG 2000 Lossless), and JPLY (JPEG Lossy). In some embodiments, the requests 374 for medical imaging reports received from the imaging selection device 133 may be stored in memory 228 of the distribution device 190.

Once the requests 374 for medical imaging reports are received, the requests 374 are processed by the allocation engine 300. The allocation engine 300 may be configured to, in conjunction with the processor 226, allocate the requests 374 to queues associated with radiologist computers 171A, 171B, 171N based on a plurality of criteria, as discussed further herein. The radiologists may use the radiologist computers 171A, 171B, 171N to generate report files 376 (also referred to herein as "medical imaging reports"). The radiologist computers 171A, 171B, 171N may transmit the report files 376 back to the distribution device 190 via links 193. In some embodiments, the report files 376 may be stored in memory 228 of the distribution device 190. The report files 376 may be routed back to the appropriate imaging selection device 133 that initiated the request for a particular report file.

When received by the imaging selection device 133, the imaging selection device 133 may translate the report file into a storing format that can be written back to the care system (not shown) (e.g., PACS, EMR storage, and/or RIS) of the particular medical facility that took the medical imaging. The translated report file may then be written to the care system. Writing the translated report to the care system may include accessing one or more patient identifier so that the correct patient's EMR can be updated with the report file from the radiologist.

Figure 4:
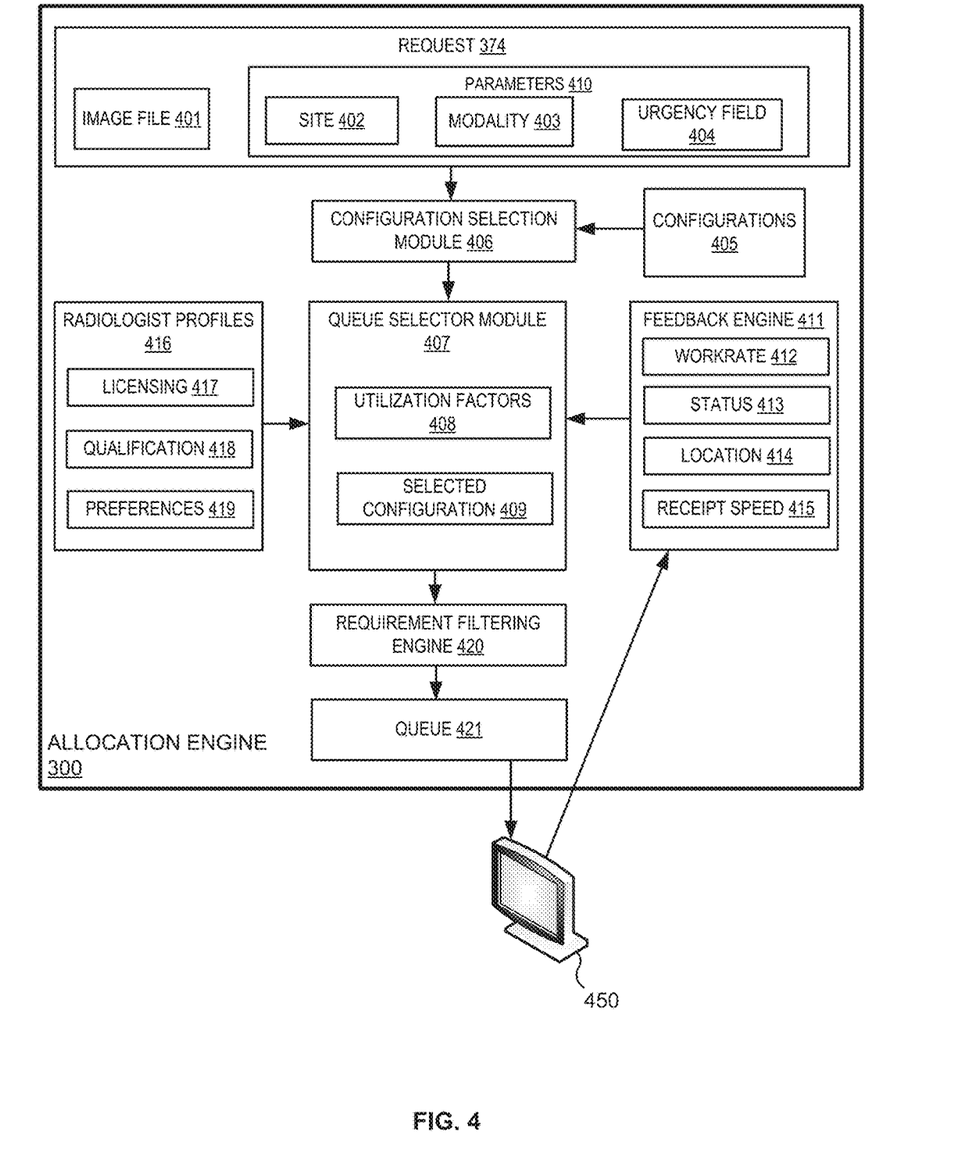
FIG. 4 is a system diagram illustrating an allocation engine of a distribution device according to some embodiments of the invention.

FIG. 4 is a system diagram illustrating an allocation engine 300 of a distribution device according to some embodiments of the invention. Allocation engine 300 may be configured to assign incoming requests for medical imaging report files to different radiologist computers by placing them in different queues for the respective radiologist computers based on a plurality of criteria. In allocation engine 300, a request 374 for a medical imaging report is received. The request 374 may be received from an imaging selection device, for example. The request 374 may be stored in memory of the distribution device. The request 374 may include at least one image file 401 and a plurality of parameters 410, such as a site 402 of the body shown in the image file 401, and an urgency field 404 defining urgency of the report file. The site 402 may be, for example, "head", "left knee", "right hand", "abdomen", etc. The urgency field 404 may include any textual, numerical, and/or graphical indicator of urgency and/or turnaround time needed for the report file such as, for example, "high", "normal", "low", "critical", "1/10", "5/10", "10/10", "1 hour", "1 day", "1 week", and the like. The request 374 may also include any of a number of additional parameters 410, such as modality 403, patient name, medical facility, and the like.

The request 374 may be fed into a configuration selection module 406. The configuration selection module 406 may have access to a plurality of configurations 405 stored in memory. Each configuration 405 may define a plurality of rules to be applied to the parameters in the request 374. The configuration selection module 406 may select the configuration based one or more of the parameters, such as the site 402 and the urgency field 404. For example, a site 402 of a "left ankle" and an urgency field 404 of "low" may return a first configuration 405 defining a first set of rules. The first set of rules may specify that the site 402 should be weighted 50% in selecting a radiologist and associated queue, and the modality 403 (e.g., X-ray) should be weighted 50%, without considering any other parameters. In another example, a site 402 of "head" and an urgency field 404 of "critical" may return a second configuration 405 defining a second set of rules. The second set of rules may be different than the first set of rules due to their differing parameters. For example, the second set of rules may specify that the site 402 should be weighted 70% in selecting a radiologist and associated queue, and the urgency field 404 of "critical" should be weighted 30%, without considering any other parameters.

The configuration selection module 406 may provide the request 374 including the image file 401 and the selected configuration 405 to the queue selector module 407. The queue selector module 407 may be configured to determine to which queue to assign the request 374. The queue selector module 407 may determine utilization factors 408 associated with the queues. For example, the queue selector module 407 may analyze the status 413 received from a plurality of radiologist computers 450. The utilization factors may include availability of radiologist computers associated with queues (e.g., whether it is within a radiologist's working hours, whether the radiologist computer is online, whether the radiologist computer is marked as available, the length of the queue associated with the radiologist, etc.). In some embodiments, each radiologist computer may indicate its status using a software button in a browser running on an operating system of radiologist computer 450. The status options may include "active" (e.g., ready to read and analyze requests for the foreseeable future), "stop" (e.g., finishing analyzing requests in the existing queue), and/or "hard stop" (e.g., stopping work; requests in existing queue should be sent back to the distribution device for redistribution). The queue selector module 407 may narrow the queues to a subset by applying the utilization factors 408 (e.g., excluding queues associated with radiologists that have a "stop" or "hard stop").

When a radiologist selects a "stop" feature in the browser interface, queue selector module 407 may stop distributing requests 374 to the queue associated with that radiologist, but may allow the radiologist to complete the requests 374 already in the queue. Any unprocessed requests 374 left in the queue may be put back into a pool of requests to be allocated. When a radiologist logs off or selects a "hard stop" feature in the interface, the queue associated with that radiologist may be cleared and the requests 374 in the queue may be put back into a pool for redistribution by the queue selector module 407. In some embodiments, after a queue is flushed (i.e., after the requests in a queue are put back into the pool), the queue selector module 407 may continue to load balance the queues. The queues may be load balanced in that each queue is expected to take the same amount of time to process.

The queue selector module 407 may further apply the selected configuration 405 to the request 374 to narrow the queues. Thus, in the first example above, the queue selector module 407 may narrow the queues to those associated with radiologists experienced in reviewing ankle X-rays. In the second example above, the queue selector module 407 may narrow the queues to those associated with radiologists experienced in reviewing head imaging that can generate the report file quickly (e.g., a radiologist computer that has a short queue, has a quick turnaround time, has a high connection speed, etc.).

In these examples, the data regarding the radiologists (e.g., experience, etc.) may be retrieved from a datastore storing radiologist profiles 416. The radiologist profiles 416 may include the profiles of each radiologist associated with a queue. Each radiologist profile 416 may include licensing data 416, qualification data 418, and preference data 419. Other profile factors may also be included in the radiologist profiles 416. Licensing data 417 may include the jurisdictions (e.g., states) in which a particular radiologist is licensed. Qualification data 418 may include the modalities and/or sites (e.g., body parts or regions) in which the radiologist is qualified (e.g., best suited, experienced, etc.) to analyze. Preference data 419 may include certain radiology preferences with regard to modality and site. Preference data 419 may correspond to a medical specialty and/or experience level associated with a particular body part or region and/or modality. For example, a particular radiologist may have significant training and experience in reading brain MRIs. The radiology may be especially qualified and/or efficient in reading certain types of image files 401.

Queue selector module 407 has access to the radiologist profiles 416 and may use licensing data 417, qualification data 418, and/or preference data 419 in assigning the request 374 to a queue corresponding to a radiologist computer 450. The licensing data 417 and qualification data 418 may include "hard rules", e.g., unqualified to read brain Mills, that may be strictly enforced where requests 374 that include a modality 403 of MRI and a site 402 of head will never be assigned. The preferences 419 may include "soft rules" of sites (e.g., body regions), such as "prefer knees, ankles, hands, and shoulders", and/or modalities that a radiologist may have experience and/or efficiency at analyzing to generate report files. The "soft rules" of preferences 419 may make it more likely that a radiologist receives their preferred requests for report files.

After the queue selector module 407 selects a subset of queues based on the utilization factors 408 and the selected configuration 409, the queue selector module 407 may provide a listing of the subset of queues to the requirement filtering engine 420. The requirement filtering engine 420 may prioritize or filter the queues in the subset of queues based on requirements of the allocation engine 300 to select a particular queue and/or requirements of each queue to stage report files, as discussed further herein. The requirement filtering engine 420 may allocate the request 374 to the selected queue 421. When the request 374 is reached in the queue 421, the request 374 may be transmitted to the radiologist computer 450. The radiologist computer 450 may then generate a report file based on the request 374.

The radiologist computer 450 may also provide feedback to the allocation engine 300 that may be input into the queue selector module 407 in order to select a queue 421 for a request 374. For example, a radiologist may long on to a browser-based interface running on the radiologist computer 450 and select an "active" software button. The "active" status may be communicated to feedback engine 411 as feedback. Feedback engine 411 may note the "active" status in status data 413.

Feedback transmitted to the feedback engine 411 may also include the location data 414 associated with the radiologist computer 450, as discussed further herein. The location data 414 may be used to limit requests 374 to queues associated with a particular geographical location, in some embodiments. Feedback transmitted to the feedback engine 411 may also include a receipt speed 415 of requests 374 received from the allocation engine 300 of the distribution device. The receipt speed 415 may correspond to a bandwidth (e.g., bits per second) of the network connection between the radiologist computer 450 and the allocation engine 300 of the distribution device.

Feedback engine 412 may also receive an request workrate 412 of a radiologist computer 450 that is reading requests. A first radiologist may analyze and generate a report file every two minutes in a particular session, while a second radiologist may analyze and generate a report file every four minutes in a particular session. The first radiologist would have a workrate of thirty orders per hour, while the second radiologist would have a workrate of fifteen orders per hour. The workrate may differ between radiologists who are reading different scan modalities or different body regions that are more complicated or include multiple images to analyze. The workrate may be measured by the distribution device in a variety of ways. For example, when the radiologist generates a report file, it may be sent back to the distribution device so that the distribution device can send the report file back to the imaging selection device or the medical care facility that is caring for the patient. In this case, the distribution device may calculate how many report files per hour are being received from a particular radiologist using one of the radiologist computers 450. The distribution device may "look back" for a particular time period (e.g., hours, days, months, etc.) to determine a workrate 412 of a particular radiologist. Feedback engine 411 may use a historical performance of a radiologist to establish a weighting factor, in some embodiments. The weighting factor may be used as an input to the queue selector module 407. In some embodiments, the workrate 412 is saved to a radiologist profile 416.

In some embodiments, the allocation engine 300 may select an upper-threshold limit for a given queue based on a variety of factors. The upper-threshold limit may differ from queue to queue. In some embodiments, the upper-threshold limit of a given queue is limited by a geolocation of a connection determined from the location 414. In some embodiments, the upper-threshold limit of a given queue is limited by a receipt speed 415 of a radiologist computer 450 that receives the queue. The upper-threshold limit may be limited by a weighting factor that is based on a workrate 412 of a particular radiologist, so as not to assign to many requests 374 to one particular queue.

In some embodiments, the upper-threshold limit assigned to each queue is normalized so that the request 374 is assigned to the queue that will be read by a radiologist the soonest, after factoring in the inputs (e.g., parameters 410, configuration 405, radiologist profiles 416, and/or feedback from feedback engine 411). Thus, although different queues may have different amounts of requests in them, the queue selector module 407 may distribute the requests 374 across queues so that each request is assigned to the queue that is predicted to complete a report file the soonest.

Figure 5:
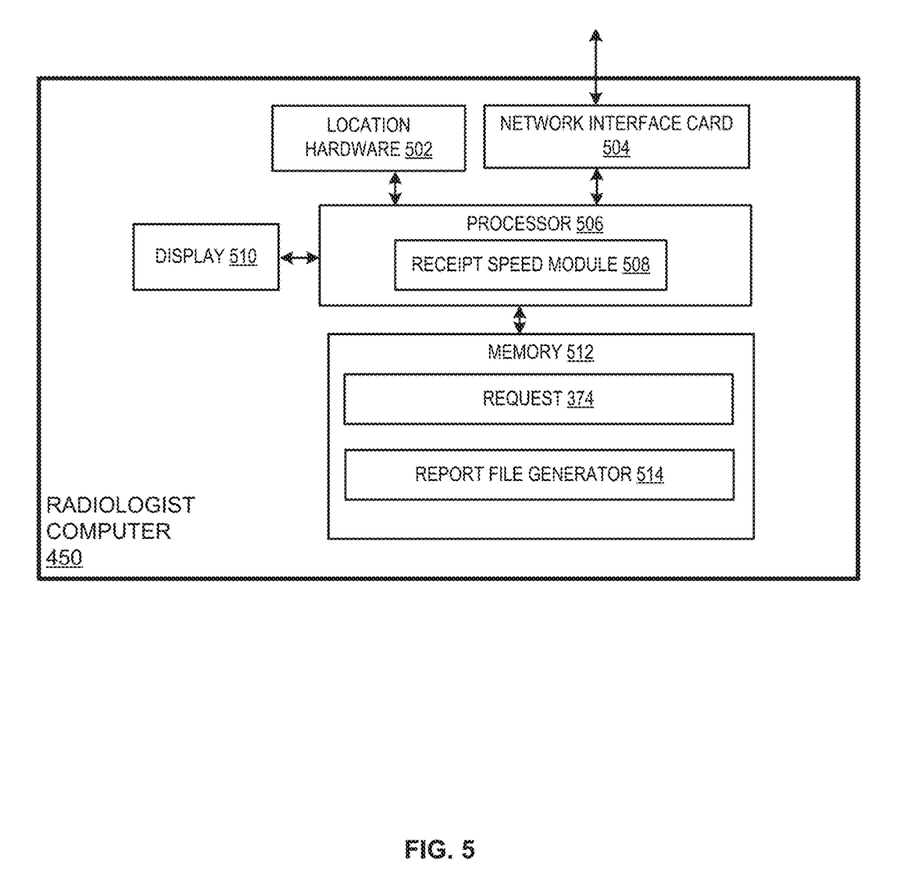
FIG. 5 is a system diagram illustrating a radiologist computer according to some embodiments of the invention.

FIG. 5 is a system diagram illustrating a radiologist computer 450 according to some embodiments of the invention. Radiologist computer 450 may be used to implement any of radiologist computers 171A, 171B, and/or 171N. Radiologist computer 450 may include location hardware 502, a network interface card 504, a processor 506, a display 510, and a memory 512. The network interface card 504 may be used to transmit report files and/or feedback to the distribution device and/or any other systems described herein.

The processor 506 may be a processor, a microprocessor, an FPGA, or any other suitable logical device. The processor 506 may include a receipt speed module 508. The receipt speed module 508 may be configured to measure the download speed of a request for a report file by measuring the received bits over a given time period, for example. The receipt speed module 508 may be implemented in hardware or software.

In some embodiments, the processor 506 may be coupled to location hardware 502. In some embodiments, the location hardware 502 includes a global positioning satellite (GPS) device. In some embodiments, the location of the radiologist computer 450 may be communicated by processor 506 querying a GPS location from the location hardware 502 and sending GPS coordinates as location data to an allocation engine of a distribution device. In some embodiments, the radiologist computer 450 may determine its location by analyzing (e.g., geolocating) local WiFi networks identified by a WiFi interface of radiologist computer 450, using a WiFi hot spot database populated by MAC addresses associated with a particular location.

Memory 512 may be a computer-readable medium and may be volatile or nonvolatile. Memory 512 may store a request 374 if the request 374 is placed in the queue associated with the radiologist computer 450 and is received by the radiologist computer 450 via the network interface card 504. The request 374 may be displayed on the display 510 of the radiologist computer 450. Memory 512 may further store a report file generator 514. The report file generator 514 may be used to generate report files based on the request 374. The report file generator 514 may be implemented in a browser (e.g., Google Chrome) executing entirely in the application layer of a protocol stack used to communicate with any of the systems described herein. The browser may execute any of the processes described herein to allow radiologists to receive and review requests 374 and complete and transmit report files in a zero footprint system, such that only a browser as an application and, in some embodiments, a corresponding extension, as required to execute the disclosed processes. In implementations that include a zero footprint system, any of the records and/or data described herein may be stored in a memory of a server, for example. The browser may then access this content stored in the memory of the server.

Figure 6:
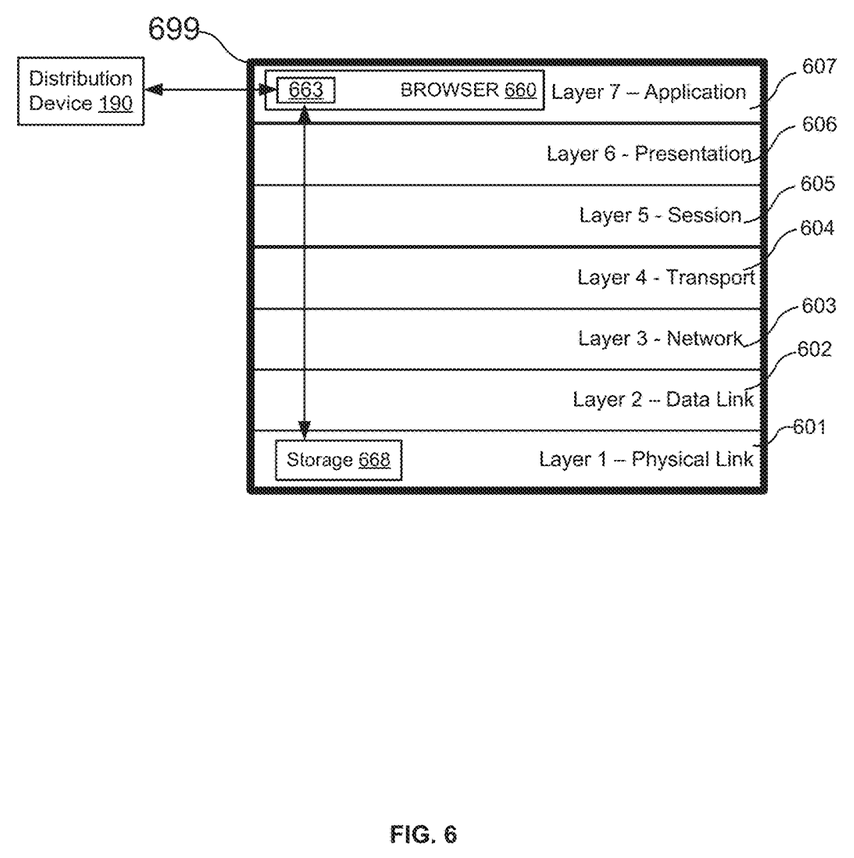
FIG. 6 is an architectural diagram illustrating the functional layers of a radiologist computer according to some embodiments of the invention.

FIG. 6 is a block diagram of a protocol stack 699 that may be implemented by the radiologist computer 450 in accordance with some embodiments. The radiologist computer 450 may implement the protocol stack to communicate with any of the other systems described herein, such as the distribution device 190. The protocol stack 699 may include one or more of seven layers: an application layer 607, a presentation layer 606, a session layer 605, a transport layer 604, a network layer 603, a data link layer 602, and a physical link layer 601. Together, these seven layers may represent a model, such as an Open Systems Interconnection (OSI) model. The OSI model of FIG. 6 may characterize the communication functions of the described systems. Although shown and described as having seven layers, it is contemplated that the protocol stack 699 may include more or fewer layers to perform less, the same, or additional functions.

According to the OSI model, the application layer 607 may interact with a user (e.g., via receiving user inputs and presenting outputs) and software applications implementing a communication component. The application layer 607 may synchronize communication between systems and determine resource availability. The application layer 607 may be application-specific, in that the specific functions dependent on the particular application being executed by the computing device.

Figure 8:
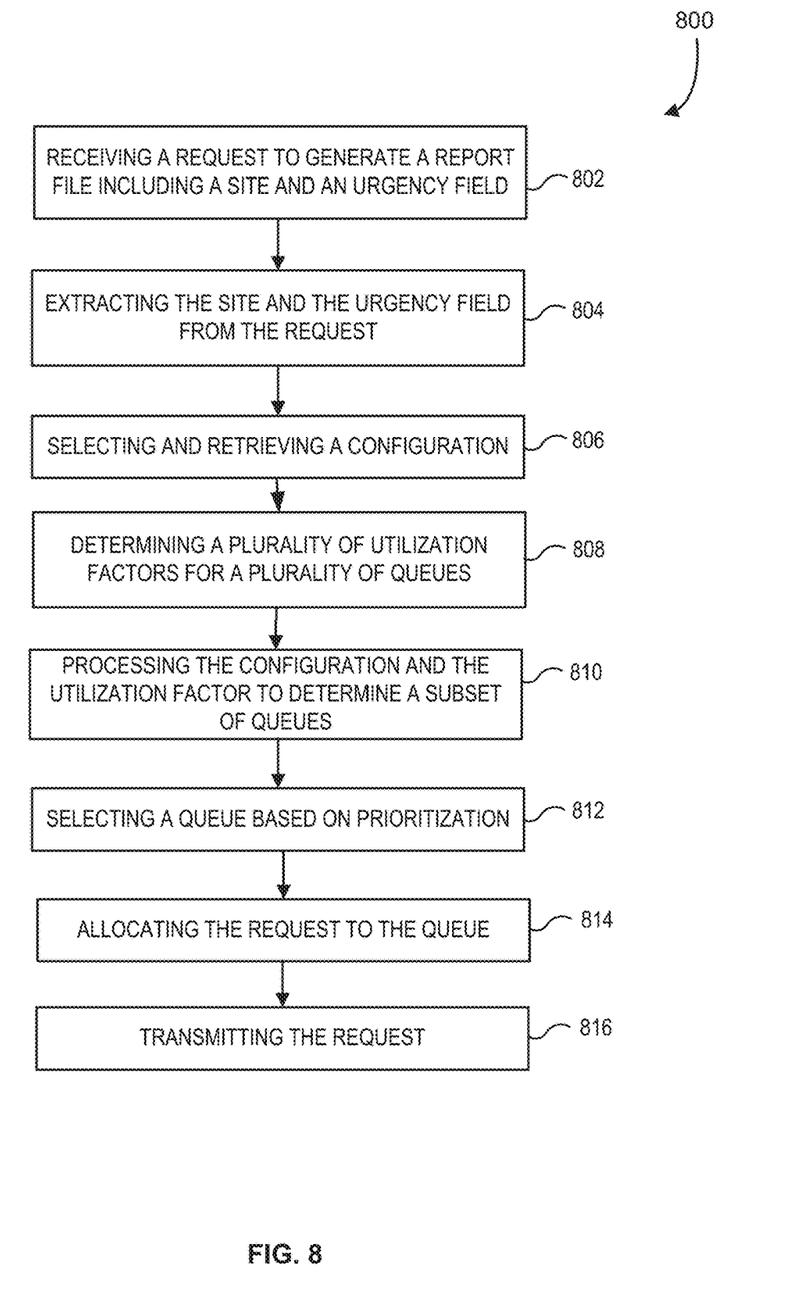
FIG. 8 is a flow chart illustrating a medical imaging distribution method according to some embodiments of the invention.

For example, the application layer 607 may execute a browser 660 (e.g., Google Chrome) which in turn may execute the processes (e.g., of flowchart 800) of the disclosure with the assistance of an extension 663. Browser 660 and extension 663 may be executed entirely at the application layer 607. This allows for radiologists to receive and view medical imaging records (e.g., from EMR storage, PACS, and/or RIS 272 (not shown)), and complete and transmit report files in a zero footprint system in that only a browser as an application and corresponding extension are required to execute the disclosed processes. In implementations that include a zero footprint system, any of the records and/or data described herein may be stored in a memory of a server, for example. The browser and corresponding extension may then access this content stored in the memory of the server.

The presentation layer 606 may translate between application and network formats. Various applications and networks may implement different syntaxes and semantics. Thus, the presentation layer 606 may transform data from the network into a form that the application accepts. The presentation layer 606 may also format and encrypt data from the application to be sent on a network.

The session layer 605 may control connections between the systems and other devices and/or servers, as described herein. The session layer 605 may establish the connections, manage the connections, and terminate the connections used to communicate between the devices.

The transport layer 604 may provide techniques for performing quality of service functions during transfers of data between devices. The transport layer 604 may provide error control. For example, the transport layer 404 may keep track of data being transmitted and transmit any communications that fail. In addition, the transport layer 604 may provide an acknowledgment of successful data transmission and send the next data to be transmitted in a synchronous fashion if no errors occurred.

The network layer 603 may provide the means of transferring the data to and from the systems over a network. The source node and destination node of the systems may each have an address which permits the other to transfer data to it by providing the address with the data. The network layer 603 may also perform routing functions that allow it to a determine a path between the source node and destination node, possibly through other nodes.

The data link layer 602 may define and provide the link between a directly and physically connected source node and destination node. The data link layer 602 may further detect and correct errors occurring at the physical link layer 601. In some embodiments, the data link layer 602 may include two sublayers: a media access control (MAC) layer that may control how devices in the network gain access to data and gain permission to transmit it, and a logical link control (LLC) layer that may identify network layer 603 protocols and encapsulate them.

The physical link layer 601 may include one or more storage devices 668. The storage devices 668 may, for example, cache study profiles for transmission, as described further herein. The physical link layer 601 may define the electrical and physical specifications of the data. The physical link layer 601 may provide a physical medium for storing unstructured raw data to be transmitted and received.

Figure 7:
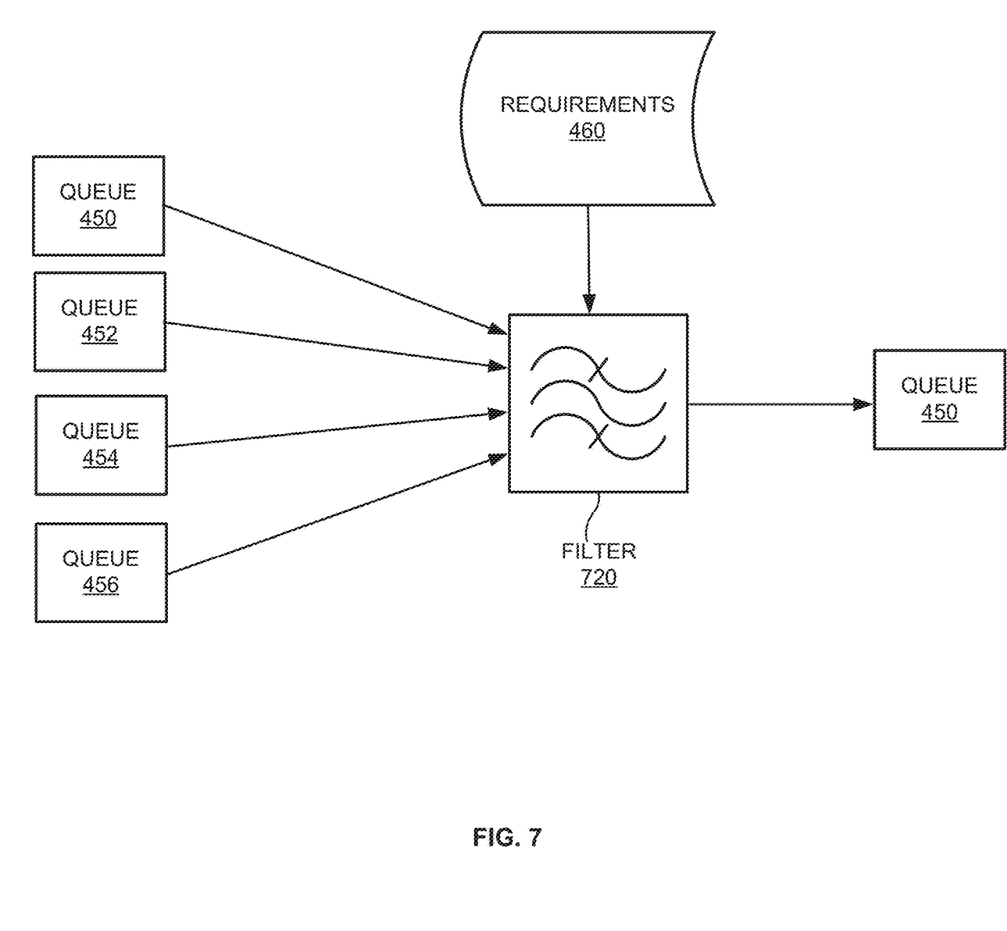
FIG. 7 is a system diagram illustrating a filter applied to radiologist computers according to some embodiments of the invention.

FIG. 7 is a system diagram illustrating a filter 720 applied to radiologist computers for selection of a queue, according to some embodiments of the invention. Filter 720 may be implemented by the requirement filtering engine 420 of FIG. 4, for example. In the illustrated example, a plurality of queues 450-456, each associated with a radiologist computer, are input into the filter 720. Although illustrated and described as having four candidate queues 450-456, it is contemplated that any number of queues may be input into filter 720.

Filter 720 may receive requirements 460. The requirements 460 may include requirements of a distribution device to allocate a certain number of requests to each queue, and/or requirements of a queue (or associated radiologist computer) to stage a certain number of report files. These requirements 460 may be applied by the filter 720 to select a single queue for distribution of the request from the plurality of queues 450-456.

For example, the distribution device may have a requirement to send ten requests to queue 450 per day (of which none have been sent), a requirement to send five requests to queue 452 per day (of which four have been sent), a requirement to send one request to queue 454 per day (of which two have been sent), and a requirement to send twenty requests to queue 456 per day (of which eighteen have been sent). Thus, the filter 720 may filter out the queues having the highest fulfillment percentages, thereby selecting queue 450 with the lowest fulfillment percentage.

In another example, queue 450 may have a requirement to stage 1,000 requests per year (of which 212 have been fulfilled), queue 452 may have a requirement to stage 500 requests per year (of which 472 have been fulfilled), queue 454 may have a requirement to stage 250 requests per year (of which 200 have been fulfilled), and queue 456 may have a requirement to stage 750 requests per year (of which 401 have been fulfilled). Thus, the filter 720 may filter out the queues having the highest fulfillment percentages, thereby selecting queue 450 with the lowest fulfillment percentage.

In some embodiments, both the requirements of the distribution device and the requirements of the queues may be considered jointly. For example, the distribution device may have a requirement to send fifteen requests to queue 450 per day (of which one has been fulfilled). Queue 452 may have a requirement to stage ten requests per day (of which nine have been fulfilled). The distribution device may have a requirement to send twenty requests to queue 454 per day (of which ten have been fulfilled). Queue 456 may have a requirement to stage five requests per day (of which three have been fulfilled). Thus, the filter 720 may filter out the queues having the highest fulfillment percentages, thereby selecting queue 450 with the lowest fulfillment percentage. The request may then be allocated to the queue 450 for generation of a report file, as described further herein.

FIG. 8 is a flow chart 800 illustrating a medical imaging distribution method, according to some embodiments of the invention. The process is illustrated as a logical flow diagram, each operation of which represents a sequence of operations that can be implemented in either hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement this process and any other processes described herein.

Some or all of the process (or any other processes described herein, or variations and/or combinations thereof) may be performed under the control of one or more computer systems configured with executable instructions and may be implemented as code (e.g., executable instructions, one or more computer programs or one or more applications). Network hardware and processing logic of distribution device 190 may execute the process blocks show in process 800, for example. The code may be stored on a computer-readable storage medium, for example, in the form of a computer program including a plurality of instructions executable by one or more processors. The computer-readable storage medium may be non-transitory.

At process block 802, a request to generate a report file may be received by a network interface of a server (e.g., distribution device 190) in a network. The request may include at least one image file and a plurality of parameters. The plurality of parameters may include a site that is imaged in the at least one image file (e.g., right knee, left ankle, left shoulder, right hand, chest, etc.). The plurality of parameters may further include a field defining urgency of the report file (e.g., "high", "normal", "low", etc.). The request may be received from a first node external to the server in the network (e.g., an imaging selection device). At process block 804, the site and the field may be extracted from the request.

At process block 806, a configuration may be selected and retrieved from a second node internal to the server. The configuration may describe a plurality of queueing rules to be executed on the plurality of parameters of the request (e.g., how queues should be selected, under which criteria the queues should be selected, how the criteria should be weighted, etc.). The configuration may be selected based on the site and the field.

At process block 808, a plurality of utilization factors may be determined for a plurality of queues. The utilization factors may be based on whether or not the queues are available, the current length of each of the queues, the processing speed of each queue, the connection speed of each queue, combinations thereof, and/or the like. In some embodiments, the utilization factors may relate to characteristics of the radiologist associated with each queue. For example, an exemplary utilization factor may be qualification data of a radiologist associated with each queue.

At process block 810, the configuration and the plurality of utilization factors may be processed to determine a subset of queues of the plurality of queues. Processing the configuration may include executing the plurality of queueing rules on the plurality of parameters included in the request. The subset of queues may be associated with a prioritization that ranks the subset of queues according to requirements of the server to select each queue and requirements of the subset of queues to stage report files. At process block 812, a queue may be selected based on the prioritization. For example, the highest priority queue may be selected. The highest priority queue may be a queue, for example, with the lowest fulfillment ratio of its requirements.

At process block 814, the request may be allocated to the queue. For example, the request may be placed at the end of the queue if the queue is ordered according to time of allocation. In some embodiments, the request may be placed in the queue according to the field defining urgency of the report file. For example, a "highly urgent" request may be placed at the front of the queue, while a "normal" or "low" request may be placed at the end of the queue.

At process block 816, the request may be transmitted to a third node external to the server in the network. The third node may correspond, for example, to a radiologist computer associated with the selected queue. The radiologist computer may use the request to generate a report file. The report file may include the at least one image file and at least one medical notation. The report file may be transmitted from the radiologist computer (i.e., at the third node) back to the server. After completion and receipt of the report file, the request may be determined from the queue.

As noted, the computer-readable medium may include transient media, such as a wireless broadcast or wired network transmission, or storage media (that is, non-transitory storage media), such as a hard disk, flash drive, compact disc, digital video disc, Blu-ray disc, or other computer-readable media. The computer-readable medium may be understood to include one or more computer-readable media of various forms, in various examples.

In the foregoing description, aspects of the application are described with reference to specific embodiments thereof, but those skilled in the art will recognize that the invention is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Where components are described as performing or being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The various illustrative logical blocks, modules, circuits, and algorithm steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined encoder-decoder (CODEC).

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

What is claimed is:

1. A device comprising:
a processor; and
a memory coupled to the processor, the memory storing instructions which when executed by the processor, cause the device to perform operations including:
receiving, by a network interface of the device in a network, a request to generate a report file, wherein the request includes at least one image file and a plurality of parameters, wherein the plurality of parameters include a site that is imaged in the at least one image file and a field defining urgency of the report file, and wherein the request is received from a first node external to the device in the network;
extracting the site and the field from the request;
selecting and retrieving, from a second node internal to the device, a configuration describing a plurality of queueing rules to be executed on the plurality of parameters of the request, wherein the configuration is selected based on the site and the field;
determining a plurality of utilization factors for a plurality of queues;
processing the configuration and the plurality of utilization factors to determine a subset of queues of the plurality of queues, wherein processing the configuration includes executing the plurality of queueing rules on the plurality of parameters included in the request, wherein the subset of queues is associated with a prioritization that ranks the subset of queues according to requirements of the device to select each queue and requirements of the subset of queues to stage report files;
selecting a queue from the subset of queues based on the prioritization;
allocating the request to the queue; and
transmitting the request to a third node external to the device in the network to generate the report file, wherein the third node is associated with the queue, and wherein the report file includes the at least one image file and at least one medical notation.

2. The device of claim 1, wherein the determining the plurality of utilization factors for the plurality of queues includes determining qualification data of a radiologist associated with each queue of the plurality of queues.

3. The device of claim 1, wherein the determining the plurality of utilization factors for the plurality of queues includes determining a processing speed associated with each queue of the plurality of queues.

4. The device of claim 1, wherein the determining the plurality of utilization factors for the plurality of queues includes determining a number of existing requests in each queue of the plurality of queues.

5. The device of claim 1, wherein the operations further include:
receiving the report file from the third node in the network.

6. The device of claim 5, wherein the operations further include:
deleting the request from the queue after receiving the report file from the third node.

7. The device of claim 1, wherein the plurality of queueing rules specify a plurality of weights for the plurality of parameters.

8. A computer-implemented method for organizing radiological imaging queues at scale, the method comprising:
receiving, by a network interface of a server in a network, a request to generate a report file, wherein the request includes at least one image file and a plurality of parameters, wherein the plurality of parameters include a site that is imaged in the at least one image file and a field defining urgency of the report file, and wherein the request is received from a first node external to the server in the network;
extracting the site and the field from the request;
selecting and retrieving, from a second node internal to the server, a configuration describing a plurality of queueing rules to be executed on the plurality of parameters of the request, wherein the configuration is selected based on the site and the field;
determining a plurality of utilization factors for a plurality of queues;
processing the configuration and the plurality of utilization factors to determine a subset of queues of the plurality of queues, wherein processing the configuration includes executing the plurality of queueing rules on the plurality of parameters included in the request, wherein the subset of queues is associated with a prioritization that ranks the subset of queues according to requirements of the server to select each queue and requirements of the subset of queues to stage report files;
selecting a queue from the subset of queues based on the prioritization;
allocating the request to the queue; and
transmitting the request to a third node external to the server in the network to generate the report file, wherein the third node is associated with the queue, and wherein the report file includes the at least one image file and at least one medical notation.

9. The computer-implemented method of claim 8, wherein the determining the plurality of utilization factors for the plurality of queues includes determining qualification data of a radiologist associated with each queue of the plurality of queues.

10. The computer-implemented method of claim 8, wherein the determining the plurality of utilization factors for the plurality of queues includes determining a processing speed associated with each queue of the plurality of queues.

11. The computer-implemented method of claim 8, wherein the determining the plurality of utilization factors for the plurality of queues includes determining a number of existing requests in each queue of the plurality of queues.

12. The computer-implemented method of claim 8, further comprising:
receiving the report file from the third node in the network.

13. The computer-implemented method of claim 12, further comprising:
deleting the request from the queue after receiving the report file from the third node.

14. The computer-implemented method of claim 8, wherein the plurality of queueing rules specify a plurality of weights for the plurality of parameters.

15. A computer-program product tangibly embodied in a non-transitory machine-readable storage medium of a computing device, including instructions that, when executed by one or more processors, cause the one or more processors to:
receive, by a network interface of the computing device in a network, a request to generate a report file, wherein the request includes at least one image file and a plurality of parameters, wherein the plurality of parameters include a site that is imaged in the at least one image file and a field defining urgency of the report file, and wherein the request is received from a first node external to the computing device in the network;
extract the site and the field from the request;
select and retrieve, from a second node internal to the computing device, a configuration describing a plurality of queueing rules to be executed on the plurality of parameters of the request, wherein the configuration is selected based on the site and the field;
determine a plurality of utilization factors for a plurality of queues;
process the configuration and the plurality of utilization factors to determine a subset of queues of the plurality of queues, wherein processing the configuration includes executing the plurality of queueing rules on the plurality of parameters included in the request, wherein the subset of queues is associated with a prioritization that ranks the subset of queues according to requirements of the computing device to select each queue and requirements of the subset of queues to stage report files;
select a queue from the subset of queues based on the prioritization;
allocate the request to the queue; and
transmit the request to a third node external to the computing device in the network to generate the report file, wherein the third node is associated with the queue, and wherein the report file includes the at least one image file and at least one medical notation.

16. The computer-program product of claim 15, wherein the determining the plurality of utilization factors for the plurality of queues includes determining qualification data of a radiologist associated with each queue of the plurality of queues.

17. The computer-program product of claim 15, wherein the determining the plurality of utilization factors for the plurality of queues includes determining a processing speed associated with each queue of the plurality of queues.

18. The computer-program product of claim 15, wherein the determining the plurality of utilization factors for the plurality of queues includes determining a number of existing requests in each queue of the plurality of queues.

19. The computer-program product of claim 15, wherein the instructions further cause the one or more processors to:
receive the report file from the third node in the network.

20. The computer-program product of claim 19, wherein the instructions further cause the one or more processors to:
delete the request from the queue after receiving the report file from the third node.

21. The computer-program product of claim 15, wherein the plurality of queueing rules specify a plurality of weights for the plurality of parameters.

* * * * *